United States Patent [19]
Papciak et al.

[11] Patent Number: 5,447,699
[45] Date of Patent: Sep. 5, 1995

[54] COMBINATION CONTAINER FOR HOLDING STERILIZED ELEMENTS AND A STERILIZABLE TRANSFER PORT

[75] Inventors: Charles Papciak, Exton; James Gerhart, West Chester; John Paproski, North Wales, all of Pa.; Kathleen A. Parker, Port Republic, N.J.; Paul Norton, Trumbauersville, Pa.; Robert Nase, Reading, Pa.; Bernard Lahendro, Spring City, Pa.

[73] Assignee: The West Company, Lionville, Pa.

[21] Appl. No.: 154,049

[22] Filed: Nov. 17, 1993

[51] Int. Cl.⁶ .......................... A61L 2/20; B65B 55/10
[52] U.S. Cl. ........................... 422/294; 53/425; 53/426; 141/85; 141/92
[58] Field of Search .......... 53/425, 426; 383/11, 383/33, 60, 211; 141/85, 89–92; 422/294, 302, 292; 312/1

[56] References Cited

U.S. PATENT DOCUMENTS

| | | | |
|---|---|---|---|
| 3,323,856 | 6/1967 | Guckel | 21/78 |
| 3,486,295 | 12/1969 | Rausing et al. | 53/89 |
| 4,118,914 | 10/1978 | Shields | 53/282 |
| 4,185,754 | 1/1980 | Julius | 383/211 X |
| 4,251,482 | 2/1981 | Sanderson et al. | 422/26 |
| 4,417,607 | 11/1983 | Scholle et al. | 141/1 |
| 4,499,932 | 2/1985 | Perigo et al. | 141/91 |
| 4,569,377 | 2/1986 | Ellis | 141/98 |
| 4,616,683 | 10/1986 | Tullis et al. | 141/98 |
| 4,622,800 | 11/1986 | Turtschan | 53/425 |
| 4,805,378 | 2/1989 | Anderson | 53/426 |
| 4,893,659 | 1/1990 | Löliger | 141/85 |
| 4,942,716 | 7/1990 | Anderson | 53/426 |
| 4,987,721 | 1/1991 | Turtschan | 53/167 |
| 5,054,260 | 10/1991 | Herzog | 53/307 |
| 5,123,229 | 6/1992 | Dardaine et al. | 53/426 |
| 5,130,093 | 7/1992 | Wieczorek | 422/26 |
| 5,217,053 | 6/1993 | Foster et al. | 141/98 |
| 5,238,660 | 8/1993 | Dietwart | 422/295 |

*Primary Examiner*—Robert J. Warden
*Assistant Examiner*—E. Leigh Dawson
*Attorney, Agent, or Firm*—Panitch Schwarze Jacobs & Nadel

[57] ABSTRACT

The present invention relates to a combination container for holding sterilized elements and a sterilizable transfer port for transferring the sterilized elements into an isolation system having a wall. The container includes a flexible bag defining a cavity containing a plurality of the sterilized elements. The container also includes a collar which has an interior surface defining a bore extending through the collar. The bag is secured to the collar with the opening in registry with the bore. A removable seal is movable between a first position where the seal initially extends across the bore to prevent elements from being removed from the cavity and to maintain the sterility of the elements and a second position where the seal is moved from the first position to access the cavity such that the elements are removable from the cavity through the opening and the bore. A transfer port extends through the wall of the isolation system and includes a first end, a second end and a conduit extending between the first and second ends. The collar is in releasable complementary, sealed engagement with the transfer port. A first door is movable between a first position closing the first end of the transfer port to prevent the elements from being moved into the isolation system and support against pressure from a treatment medium and a second position opening the first end of the transfer port to allow the elements to be moved into the isolation system or clean sterile area.

9 Claims, 9 Drawing Sheets

COMBINATION CONTAINER FOR HOLDING STERILIZED ELEMENTS AND A STERILIZABLE TRANSFER PORT

FIELD OF THE INVENTION

The present invention relates to a container for holding sterilized elements and, more particularly, to a combination container for holding sterilized elements and a sterilizable transfer port for transferring the sterilized elements into an isolation system or other clean sterile area.

BACKGROUND OF THE INVENTION

The pharmaceutical industry is concerned with reducing costs to meet the national demands for reasonably priced prescription drugs. One way the pharmaceutical industry is attempting to reduce costs is to modify its current methods of packaging its sterile products. In the past, the packaging of sterile products was accomplished in clean rooms wherein the machines used to package the sterilized product and the personnel necessary to operate the machines are housed. Building, operating and maintaining large clean rooms is quite expensive and significantly contributes to overhead costs.

Thus, a need has arisen for a locally controlled environment wherein a barrier is positioned around the precise area that must be maintained clean so that a reduction in the size of the traditional clean room can be achieved. This results in a savings in capital costs, and the elimination or a reduction in number of people from the clean room, which is the biggest source of contamination.

While locally controlled environments, often referred to as isolation systems, have been known for a number of years, introducing sterilized parts into the isolation system without jeopardizing the sterility of the parts or atmosphere within the isolation system has been problematic. One attempt to solve this problem requires providing a cleaning and sterilizing machine next to the isolation system. The machine includes a hard-walled reusable treatment vessel which receives small articles, such as closure elements for pharmaceutical containers. The containers are sterilized within the treatment vessel and then the treatment vessel is coupled to the isolation system. Prior to passing the closure elements from the treatment vessel to the isolation system, the conduit between the treatment vessel and isolation system is sterilized. After sterilization is complete, the treatment vessel can be accessed to allow the closure elements to be passed through into the isolation system.

However, positioning a cleaning and sterilizing machine proximate to the isolation system, as described above, is also problematic in that it requires the pharmaceutical company to incur the capital costs of purchasing such a cleaning and sterilizing machine and to incur the operation and maintenance costs of such a machine. Therefore, a need has arisen for an inexpensive method of transferring sterilized closure elements to an isolation system.

The present invention provides a combination container for holding sterilized elements and a sterilizable transfer port for transferring the sterilized elements into an isolation system. The container is formed of a flexible bag which receives the sterilized elements and a sealed collar which can be sterilized when it is connected to the isolation system to transfer the elements from the container to the isolation system. The container and transfer port of the present invention is easily used and results in considerable savings in money as well as time in packaging sterilized products for the pharmaceutical industry.

SUMMARY OF THE INVENTION

Briefly stated, the present invention comprises a container for holding sterilized elements. The container includes a flexible bag defining a cavity containing a plurality of the sterilized elements. The bag includes an opening for removing the elements from the cavity. The container includes a collar having a bore extending therethrough. The bag is secured to the collar with the opening and the bore being in registry. A removable seal is movable between a first position wherein the seal initially extends across the bore to prevent the elements from being removed from the cavity and to maintain the sterility of the elements and a second position wherein the seal is moved from the first position to access the cavity such that the elements are removable from the cavity through the opening and the bore.

In another aspect of the present invention, the container is combined with a sterilizable transfer port for transferring the sterilized elements into an isolation system. The transfer port is generally tubular and extends through a wall of the isolation system. The transfer port includes a first end, a second end and a conduit extending between the first and second ends. The collar is in releasable complementary, sealed engagement with the transfer port. At least one supply conduit is in fluid communication with the conduit for introducing into the conduit at least one treatment medium. A first door is movable between a first position closing the first end of the port to prevent the elements from being moved into the isolation system and a second position opening the first end of the port to allow the elements to be moved into the isolation system whereby when the seal is removably mounted across the bore and the first door is in the first position the seal, collar, conduit, and first bore define a chamber for receiving the treatment medium and when the seal is moved from the first position to the second position and the first door is in the second position, the elements are movable into the isolation system from said cavity through the opening, bore and conduit.

BRIEF DESCRIPTION OF THE DRAWINGS

The foregoing summary, as well as the following detailed description, will be better understood when read in conjunction with the appended drawings. For the purpose of illustrating the invention, there is shown in the drawings an embodiment which is presently preferred, it being understood, however, that the invention is not limited to the specific methods and instrumentalities disclosed. In the drawings.

DESCRIPTION OF THE PREFERRED EMBODIMENT

Certain terminology is used in the following description for convenience only, and is not limiting. The words "right," "left," "lower" and "upper" designate, directions in the drawings to which reference is made. The words "inwardly" and "outwardly" refer to directions toward and away from, respectively, the geometric center of the combination container for holding sterilized elements and a sterilizable transfer port and designated parts thereof. The terminology includes the words above specifically mentioned, derivatives thereof and words of similar import.

Referring now to the drawings in detail, wherein like numerals indicate like elements throughout, there is shown in FIGS. 1 through 9 a preferred embodiment of a combination container, generally designated 10, for holding sterilized elements 12 and a sterilizable transfer port, generally designated 14, for transferring the sterilized elements 12 into an isolation system 16 or other clean sterile area without exposing the sterilized elements to ambient atmosphere.

Figure 1:
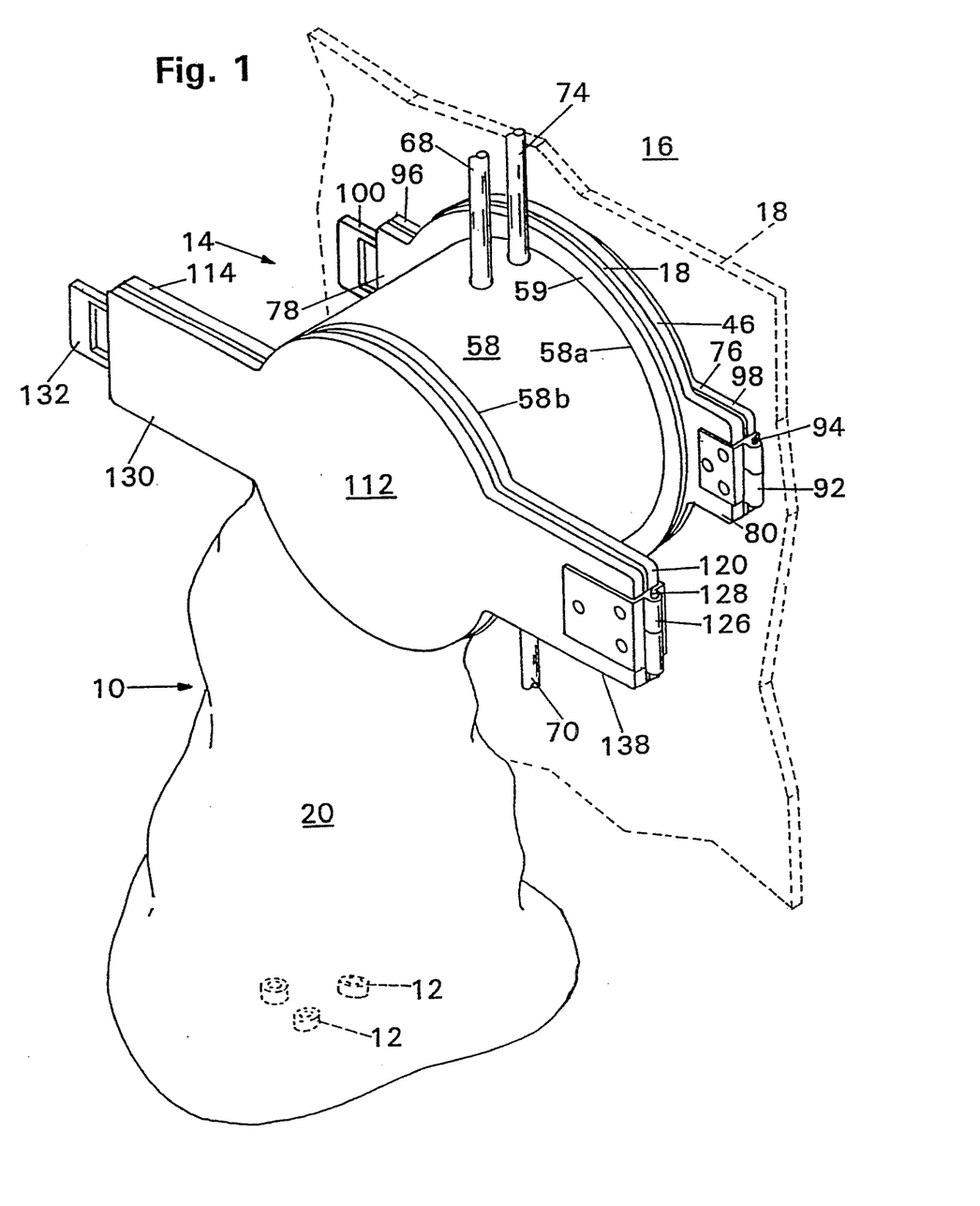
FIG. 1 is a perspective view of a combination container for holding sterilized elements and a sterilizable transfer port for transferring the sterilized elements into an isolation system in accordance with the present invention.

Referring now to FIG. 1, the isolation system 16 is only partially shown and includes a wall 18. The wall 18 forms a walled enclosure (not shown) defining a work area (not shown). A filtered inlet port (not shown) is provided in the walled enclosure for allowing air to flow into the work area. An filtered outlet port (not shown) is also provided in the walled enclosure for allowing air to flow out of the work area. An air flow control device (not shown) causes air to flow through the inlet port into the work area and out of the enclosure work area through the outlet port to maintain a clean environment within the isolation system. Isolation systems and clean sterile areas are well known to those of ordinary skill in the art and, therefore, further description thereof is omitted for purposes of convenience only, and is not limiting.

The present invention is directed to transferring the sterilized elements 12 into the isolation system 16 while maintaining the sterility of the sterilized elements 12 and the cleanliness of the isolation system 16. In the present embodiment, it is preferred that the sterilized elements 12 be closure elements for pharmaceutical containers (not shown). The isolation system 16 houses a filling machine (not shown) for depositing a pharmaceutical within one or more containers. In addition, the isolation system 16 includes a sorting machine (not shown) for receiving and feeding the sterilized elements 12 into the filling machine. The feeding and filling machines are well known to those skilled in the art and, therefore, further description thereof is omitted for purposes of convenience only, and is not limiting.

Referring now to FIGS. 1 through 4, there is shown a flexible bag 20 defining a cavity 22 containing a plurality of the sterilized elements 12. While only three sterilized elements are shown in FIG. 1, the present invention is not limited to any particular number of sterilized elements 12 within the cavity 22. That is, any number of sterilized elements 12 can be placed within the cavity 22 for transferring the same into the isolation system 16, such as 100, 200, 1,000 or more without departing from the spirit and scope of the invention. The bag 20 includes an opening 24 for removing the elements 12 from the cavity 22. The opening 24 is generally circular, although other shaped openings, such as square or triangular, could be used within the spirit and scope of the invention.

In the present embodiment, it is preferred that the bag 20 be constructed of a polymeric material which is steam-breathable to permit the elements 12 to be sterilized within the bag 20, such as Tyvek ® manufactured by E. I. du Pont de Nemours & Co., located in Wilmington, Del. However, it is understood by those skilled in the art from this disclosure that other materials could be used to construct the bag 20, such as polyethylene or polypropylene, without departing from the spirit and scope of the invention. It is preferred that the bag be constructed using a molding process, such as blow molding. However, it is understood by those skilled in the art from this disclosure that other methods could be used to construct the bag 20, such as woven and formed.

The present invention is not limited to constructing the shape of the cavity 22 in any particular form. That is, the cavity 22 could be generally cylindrical, square or a combination of shapes. Further, the size of the bag can be selected in accordance with the number of sterilized elements 12 which are to be located within the cavity 22. Further, the bag 20 could be in the form of an elongate tube closed at its distal end and having a plurality of smaller bags (not shown) therein connected in series, each including a plurality of sterilized elements, such that the plurality of bags could be pulled through the opening 24 of the bag 20 one by one as needed.

Figure 2:
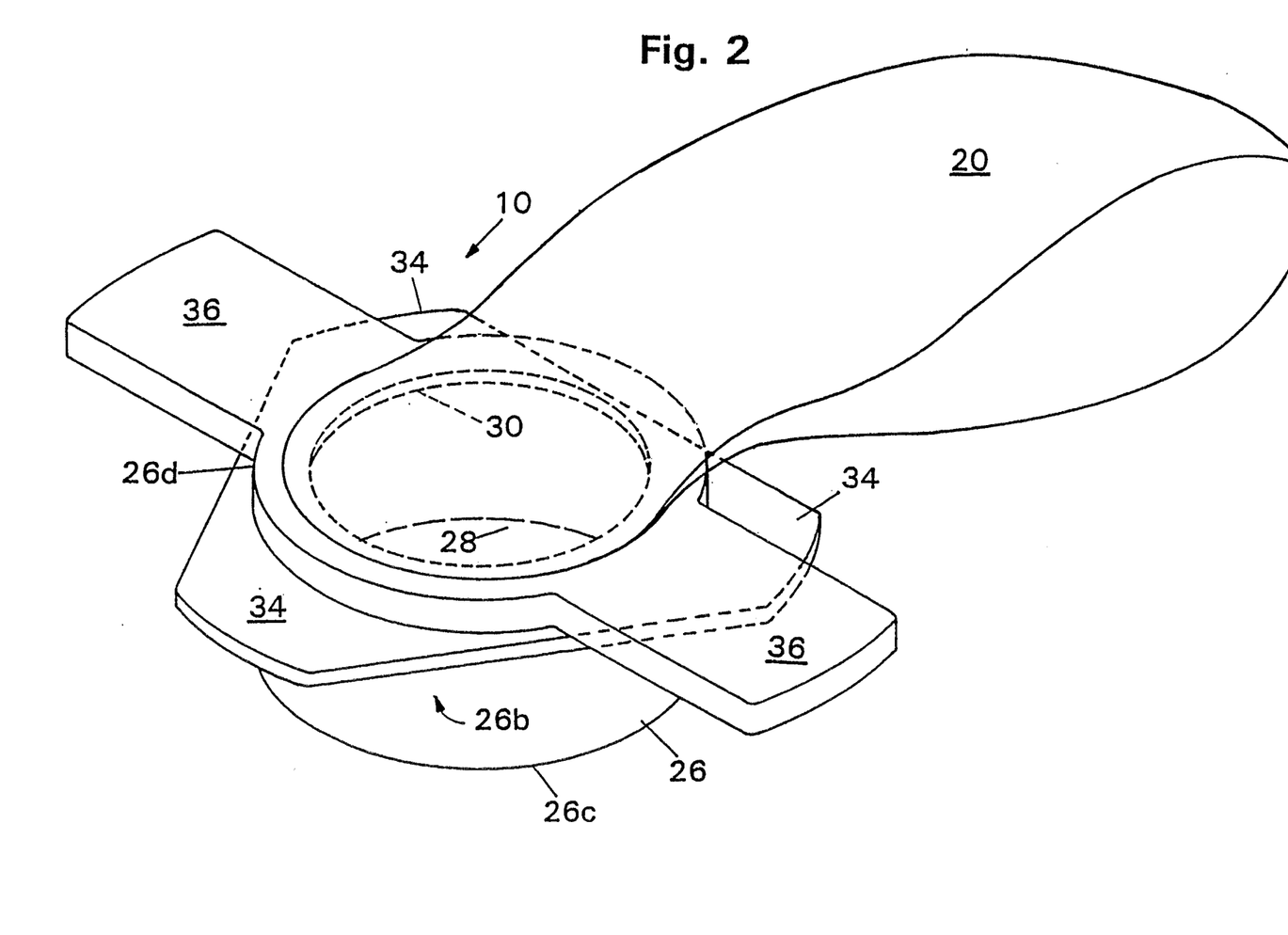
FIG. 2 is a perspective view of a collar of the container shown in FIG. 1 in accordance with the present invention.
Figure 3:
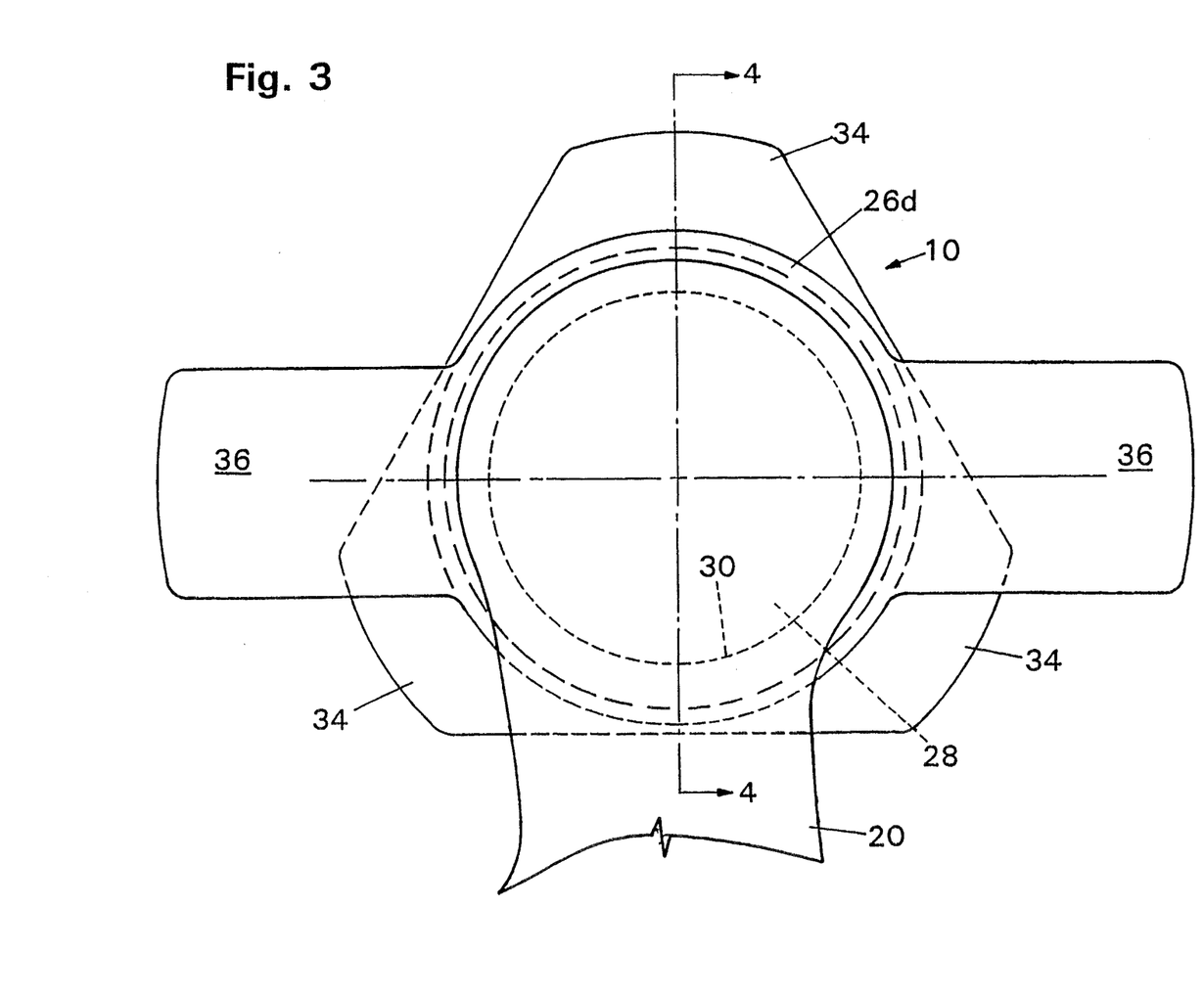
FIG. 3 is a top plan view of the collar shown in FIG. 2.
Figure 4:
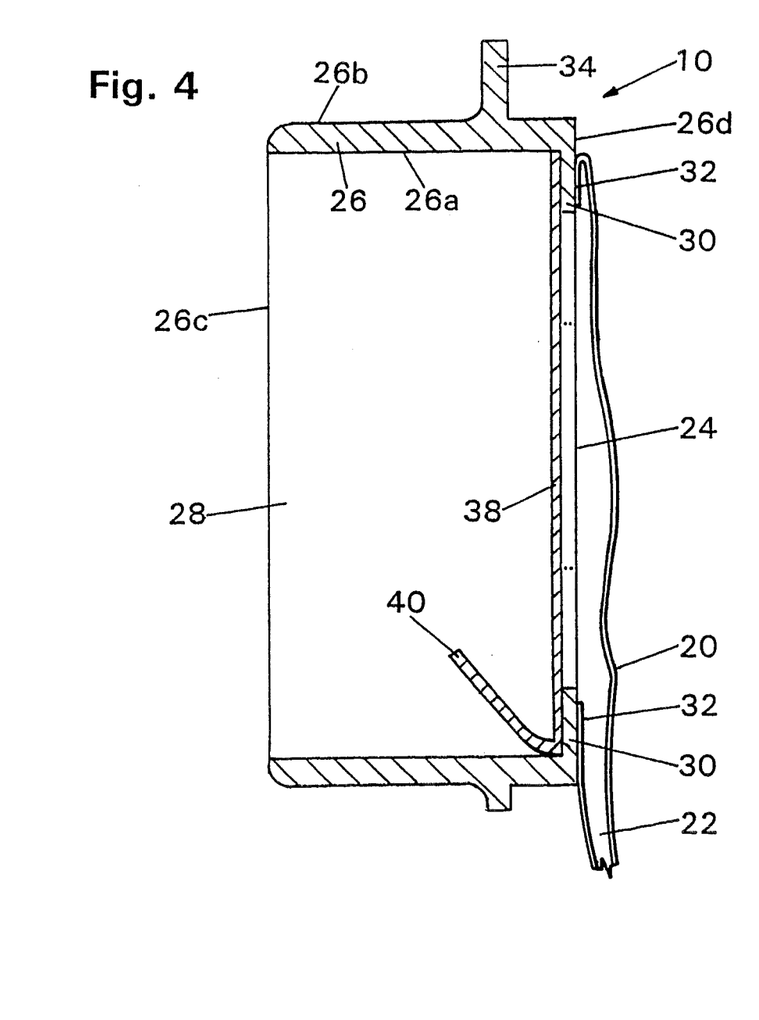
FIG. 4 is a cross-sectional view of the collar shown in FIG. 3, taken along lines 4—4 of FIG. 3.

Referring now to FIGS. 2 through 4, the container 10 includes a collar 26 having an interior surface 26a, an exterior surface 26b, a first end 26c and a second end 26d. The interior surface 26a defines a bore 28 extending through the collar 26. The collar 26 is preferably generally annular in cross section, although other shapes could be utilized, such as generally square, rectangular or triangular, so long as the collar 26 can be complementarily mated to the transfer port 14, as described in more detail hereinafter. As best seen in FIGS. 3 and 4, the bore 28 is generally cylindrically shaped.

The collar 26 preferably includes a flange 30 extending radially inwardly from the interior surface 26a of the collar 26 proximate the second end 26d of the collar 26. The flange 30 preferably extends generally perpendicularly with respect to the interior surface 26a of the collar 26. However, it is understood by those skilled in the art in view of this disclosure that the flange 30 could extend at another angle with respect to the interior surface 26a of the collar 26, such as 60°, 70° or 80°, without departing from the spirit and scope of the invention.

As best shown in FIG. 4, the bag 20 is secured to the collar 26 with the opening 24 in registry with the bore 28. More particularly, a proximal portion 32 adjacent the opening 24 of the bag 20 is secured to the flange 30 such that the sterilized elements 12 within the cavity 22 can be passed from the cavity 22 through the opening 24 and bore 28. The particular manner in which the bag 20 is secured to the collar 26 is not pertinent to the present invention, but it is preferred that the proximal portion 32 be heat sealed to the flange 30. With the bag 20 secured to the collar 26, the bag 20 hangs downwardly from the collar 10 due to the force of gravity.

While in the present embodiment, it is preferred that the proximal portion 32 of the bag 20 be heat sealed to the flange 30 of the collar 26, it is understood by those skilled in the art from this disclosure that there are other methods for securing the proximal portion 32 of the bag 20 to the collar 26. For instance, the proximal portion 32 could be sized to correspond to the exterior surface 26b of the collar 26 and a clamp could be used to extend around the exterior surface 26b the collar 26 to secure the proximal portion 32 of the bag 20 to the collar 26 or the proximal portion 32 could be adhesively secured to the flange 30, without departing from the spirit and scope of the invention.

Referring now to FIGS. 2 and 3, the container 10 further includes at least one interlocking element on the collar 26 for quickly connecting and disconnecting the collar 26 to the transfer port 14. In the present embodiment, it is preferred that the container 10 include three interlocking elements 34 extending radially outwardly from the exterior surface 26b of the collar 26 and spaced equidistantly thereabout. As best shown in FIG. 3, the three interlocking elements 34 cooperate to be generally in the form of a triangle having its corners truncated. The purpose of the interlocking elements 34 and their cooperation with the transfer port 14 are described in more detail hereinafter.

Referring now to FIGS. 2 and 3, the collar 26 includes a pair of handles 36 which extend radially outwardly from the exterior surface 26b of the collar 26 between the interlocking elements 34 and the bag 20. The handles 36 extend in diametrically opposite directions and are used to rotate the container 10 during attachment of the container 10 to the transfer port 14, as described in more detail hereinafter. However, it is understood by those of ordinary skill in the art from this disclosure that other types of handles could be attached to the collar 26, such as screw on cabinet handles.

In the present embodiment, it is preferred that the collar 26, interlocking elements 34 and handles 36 be constructed of a high strength light weight material. For instance, a polymeric material such as polypropylene could be used. However, it is understood by those skilled in the art that other materials could be used, such as stainless steel, to construct the collar 26, interlocking elements 34 and handles 36, without departing from the spirit and scope of the invention. Similarly, it is preferred that the collar 26, interlocking elements 34 and handles 36 be constructed by a molding process, such as injection molding, as an integral piece. However, it is understood by those skilled in the art that other manufacturing processes could be used to manufacture the collar 26, interlocking elements 34 and handles 36, such as other molding and finishing methods, without departing from the spirit and scope of the invention. While it is preferred that the collar 26, interlocking elements 34 and handles 36 be constructed as an integral piece, it is understood by those skilled in the art that the same could be separate pieces which are interlocked together.

Referring now to FIG. 4, there is shown a removable seal 38 movable between a first position (shown in FIG. 4) wherein the seal 38 initially extends across the bore 28 to prevent the sterilized elements 12 from being removed from the cavity 22 and to maintain the sterility of the sterilized elements 12 (only shown in FIG. 1) and a second position (not shown) wherein the seal 38 is moved from the first position to access the cavity 22 such that the sterilized elements 12 are removable from the cavity 22 through the opening 24 and the bore 28. More particularly, the seal 38 is in partial facing engagement with the portion of the flange 30 facing away from the bag 20 when the seal 38 is in the first position.

It is preferred that the seal 38 be releasably adhesively secured to the flange 30 when the seal 38 is in the first position and include a pull tab 40 for assisting in removing the seal 38 from the flange 30. Prior to attaching the seal 38 to the flange 30, the seal 38 and flange 30 must be sterilized. When the pull tab 40 is used to remove the seal 38 from the flange 30, the seal 38 is in the second position wherein the sterilized elements 12 within the cavity 22 can be accessed. That is, the seal 38 is in the second position when it is at least partially removed from the flange 30 to access the cavity 22 of the bag 20. While it is preferred that the seal 38 be positioned across the flange 30, it is understood that the seal 38 could be positioned anywhere within the bore 28, such as proximate the first end 26c of the collar 26 without departing from the spirit and scope of the invention.

In the present embodiment, it is preferred that the seal 38 be constructed of a polymeric material which is steam breathable, such as Tyvek ®. The seal 38 preferably includes a peel-away backing to expose an adhesive surface (not shown) which can be attached to the flange 30 during assembly of the container 10. The pull tab 40 is preferably integrally formed with the seal 38. While it is preferred that the seal 38 be constructed of a steam-breathable polymeric material, it is understood by those skilled in the art from this disclosure that other materials could be used to construct the seal 38, such as metalized foil or plastic.

Figure 5:
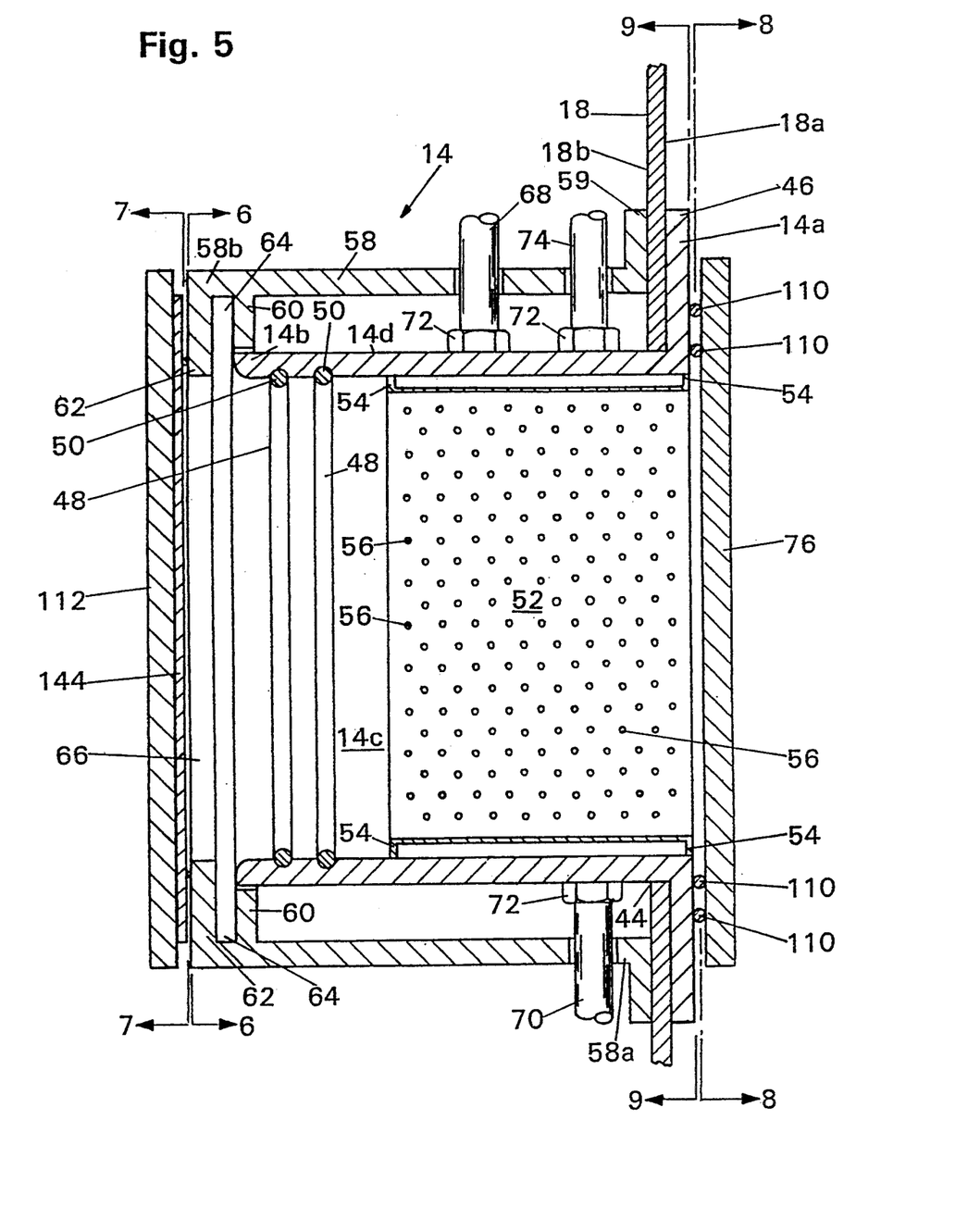
FIG. 5 is a cross-sectional view of the transfer port shown in FIG. 1.

Referring now to FIGS. 1 and 5, the transfer port 14 is generally tubular and extends through the wall 18 of the isolation system 16. The transfer port 14 includes a first end 14a and a second end 14b. The first end 14a is positioned on the side of the wall 18 within the isolation system 16. The second end 14b located on the side of the wall 18 externally of the isolation system 16. The transfer port 14 further includes an interior surface 14c and an exterior surface 14d. More particularly, the wall 18 includes an aperture 44 for complementarily receiving the first end 14a of the transfer port 14. In the present embodiment, it is preferred that the aperture 44 be generally circular to receive the transfer port 14. A flange 46 extends radially outwardly from the first end 14a of the transfer port 14 and is in facing engagement with the interior surface 18a of the wall 18.

The interior surface 14c of the transfer port 14 defines a conduit 42 extending between the first and second ends 14a, 14b. The conduit 42 is generally cylindrically shaped and sized to complementarily receive the collar 26. That is, the exterior surface 26b of the collar 26 is in releasable complementary, facing, sealed engagement with the interior surface 14c of the transfer port 14. Positioned within the conduit 42 proximate the second end 14b of the transfer port 14 are a pair of elastomeric o-rings 48 which are disposed within grooves 50 formed within the interior surface 14c of the transfer port 14. The o-rings 48 provide a fluid-tight connection between the interior surface 14c of the transfer port 14 and the exterior surface 26b of the collar 26 when the collar 26 is positioned within the transfer port 14. While in the present embodiment, it is preferred that a pair of o-rings 48 be used to provide a fluid seal between the collar 26 and transfer port 14, it is understood by those skilled in the art that other types of sealing devices, such as a gasket, can be used without departing from the spirit and scope of the invention.

Positioned within the conduit 42 is a generally annular insert 52. The insert 52 includes a pair of radially outwardly extending flanges 54 which are in engagement with the interior surface 14c of the transfer port 14. The flanges 54 support the insert 52 within the transfer port 14 radially inwardly of the interior surface 14c. The insert 52 preferably extends from the first end 14a of the transfer port 14 through the conduit 42 to a distance from the second end 14b of the transfer port 14 which corresponds to the length of the collar 26 between the first end 26c of the collar and the interlocking elements 34. The insert 52 includes a plurality of apertures 56 for allowing a treatment medium, such as steam, to pass therethrough. The purpose of the insert 52 is to prevent the treatment medium from collecting on the interior surface 14c of the transfer port 14 and potentially contaminating any sterilized elements 12.

In the present embodiment, it is preferred that the transfer port 14 be constructed of a high-strength, lightweight material, such as stainless steel. However, it is understood by those skilled in the art that other materials could be used to construct the transfer port 14, without departing from the spirit and scope of the invention. In the present embodiment, it is preferred that the insert 52 and the other elements described hereinafter be constructed of the same material as the transfer port 14 unless otherwise stated. Although, it is understood by those skilled in the art that other materials could be used, if desired.

While in the present embodiment it is preferred that the transfer port 14 be generally annular shaped in cross-section, it is understood by those skilled in the art that the transfer port 14 could have any cross-sectional configuration so long as it is complementary to the cross-sectional configuration of the collar 26.

Figure 6:
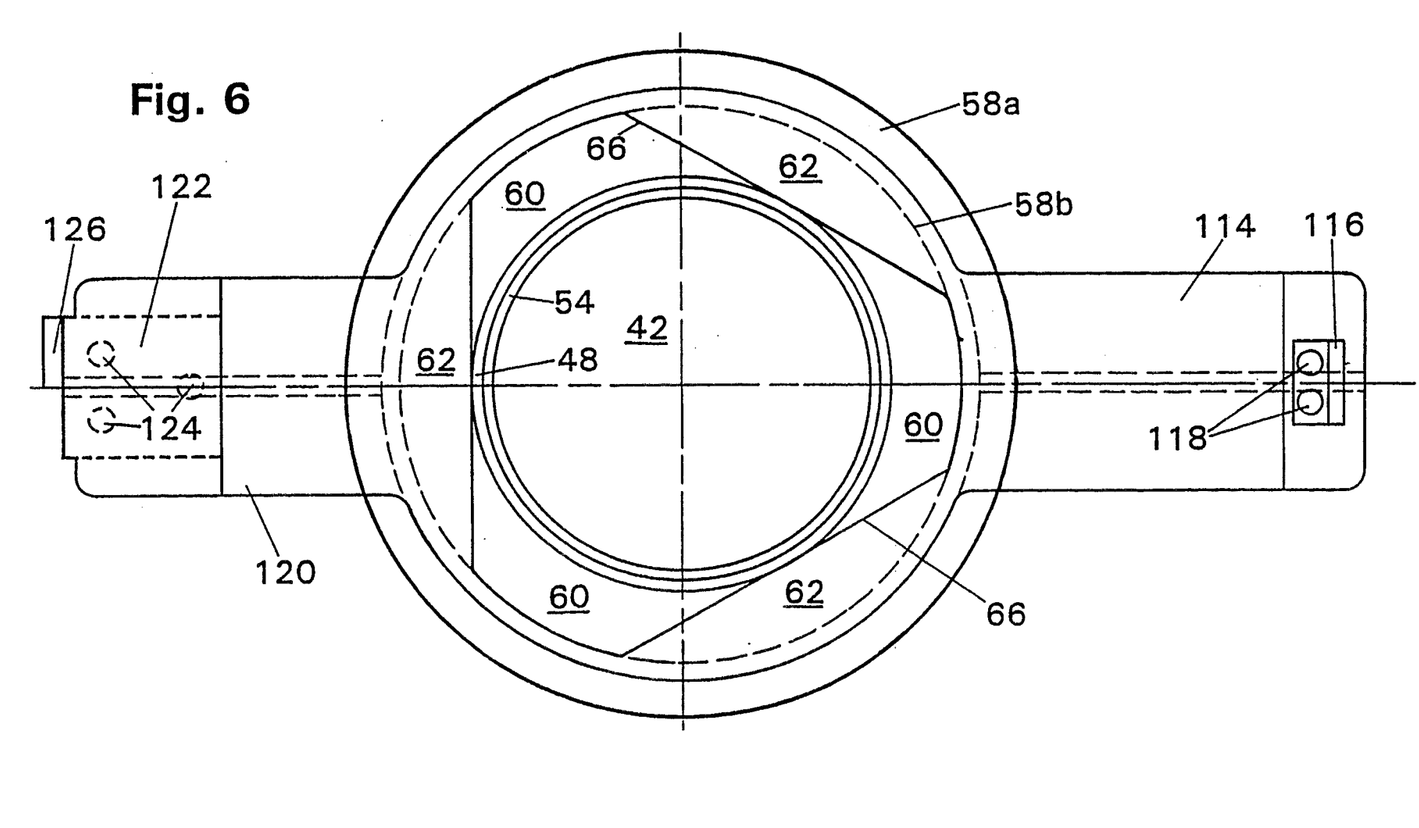
FIG. 6 is a cross-sectional view of the transfer port shown in FIG. 5, taken along lines 6—6 of FIG. 5.

Referring now to FIGS. 2, 5 and 6, a quick-connect device is interconnected between the transfer port 14 and the collar 26 for quickly connecting and disconnecting the transfer port 14 and collar 26. In the present embodiment, it is preferred that the quick-connect device comprise a bayonet-type quick connection between the collar 26 and the transfer port 14. That is, the interlocking elements 34 which extend radially outwardly from the collar 26 are configured to correspond to a female member 58 which surrounds the transfer port 14.

More particularly, the female member 58 includes a first end 58a having a flange 59 extending radially outwardly therefrom which is in engagement with the exterior surface 18b of the wall 18. The first end 58a of the female member 58, the wall 18, and the flange 44 extending from the first end 14a of the transfer port 14 all include suitably aligned apertures (not shown) for receiving standard fastening elements, such as nuts and bolts, to secure the transfer port 14 and female member 58 to the wall 18 of the isolation system 16, in a manner well understood by those skilled in the art. However, it is also understood by those skilled in the art that the transfer port 14 and female member 58 can be secured to the wall 18 of the isolation system 16 in other manners, such as by welding, without departing from the spirit and scope of the invention.

The second end 58b of the female member 58 includes a first flange 60 extending radially inwardly into engagement with the exterior surface 14d of the second end 14b of the transfer port 14. Three second flanges 62 are spaced from the first flange 60 and extend radially inwardly from the second end 58b of the female member 58 to define a groove 64 therebetween. The groove 64 is sized to complementarily receive the interlocking members 34, as described in more detail hereinafter. The second flanges 62, as best shown in FIG. 6, define an aperture 66 for receiving the interlocking elements 34. That is, the profile of the interlocking elements 34 is selected to match the aperture 66 defined by the second flanges 62.

To quickly connect the collar 26 to the transfer port 14, the collar 26 is grasped by the handles 36 and the first end 26c of the collar 26 is inserted into the conduit 42 through the aperture 66. The collar 26 is rotated until the interlocking elements 34 are aligned with the profile of the aperture 66 defined by the second flange 62. The collar 26 is then further moved inwardly until the first end 26c of the collar 26 is positioned proximate the insert 52 and the interlocking elements 34 are aligned with the groove 64. The handles 34 are then used to rotate the collar 26 until the interlocking elements 34 are positioned within the grooves 64. At this point, the collar 26 is interlocked to the transfer port 14. Stops (not shown) can be provided within the groove 64 for limiting the range of rotation of the collar 26.

While in the present embodiment, it is preferred that the quick-connect device be a bayonet-type quick connection, it is understood by those skilled in the art that other quick-connect devices could be used without departing from the spirit and scope of the invention. For instance, a clamping mechanism or a cam-lock arrangement could be used to secure the collar 26 within the transfer port 14.

As shown in FIGS. 1 and 5, at least one supply conduit 68 and at least one discharge conduit 70 are in fluid communication with the port conduit 42 for introducing into and removing from the port conduit 42 at least one treatment medium (not shown). In the present embodiment, it is preferred that the supply conduit 68 be bolted to the transfer port 14 by a bolt 72 in a manner well understood by those skilled in the art. The supply conduit 68 supplies the treatment medium to the transfer port 14 to sterilize the same. In the present embodiment, it is preferred that the treatment medium be a sterilizing agent, such as water in pressurized steam phase. However, it is understood by those skilled in the art that other treatment mediums could be used, such as hydrogen peroxide or other sterilizing agent, without departing from the spirit and scope of the invention.

It is preferred that the discharge conduit 70 also be bolted to the transfer port 14 by a bolt 72 in a manner well understood by those skilled in the art. The discharge conduit 70 is preferably bolted to the transfer port 14 proximate its bottom to take advantage of the affects of gravity in draining the transfer port 14 of the treatment medium and any condensation. The discharge conduit 70 preferably includes a screen (not shown) for preventing foreign matter from entering the drainage system.

In the present embodiment, it is also preferred that the transfer port 14 include a vacuum or drying conduit 74 for facilitating the drying of the transfer port 14 after it has been treated with the treatment medium. The vacuum or drying conduit 74 is also preferably bolted to the transfer port 14 by a bolt 72 proximate the supply conduit 68. The supply conduit 68, discharge conduit 70 and vacuum or drying conduit 74 are all connected to appropriate systems for carrying out the intended task. The systems are not shown since they are not pertinent to the present invention and well understood by those skilled in the art and, therefore, further description thereof is omitted for purposes of convenience only and is not limiting.

Figure 8:
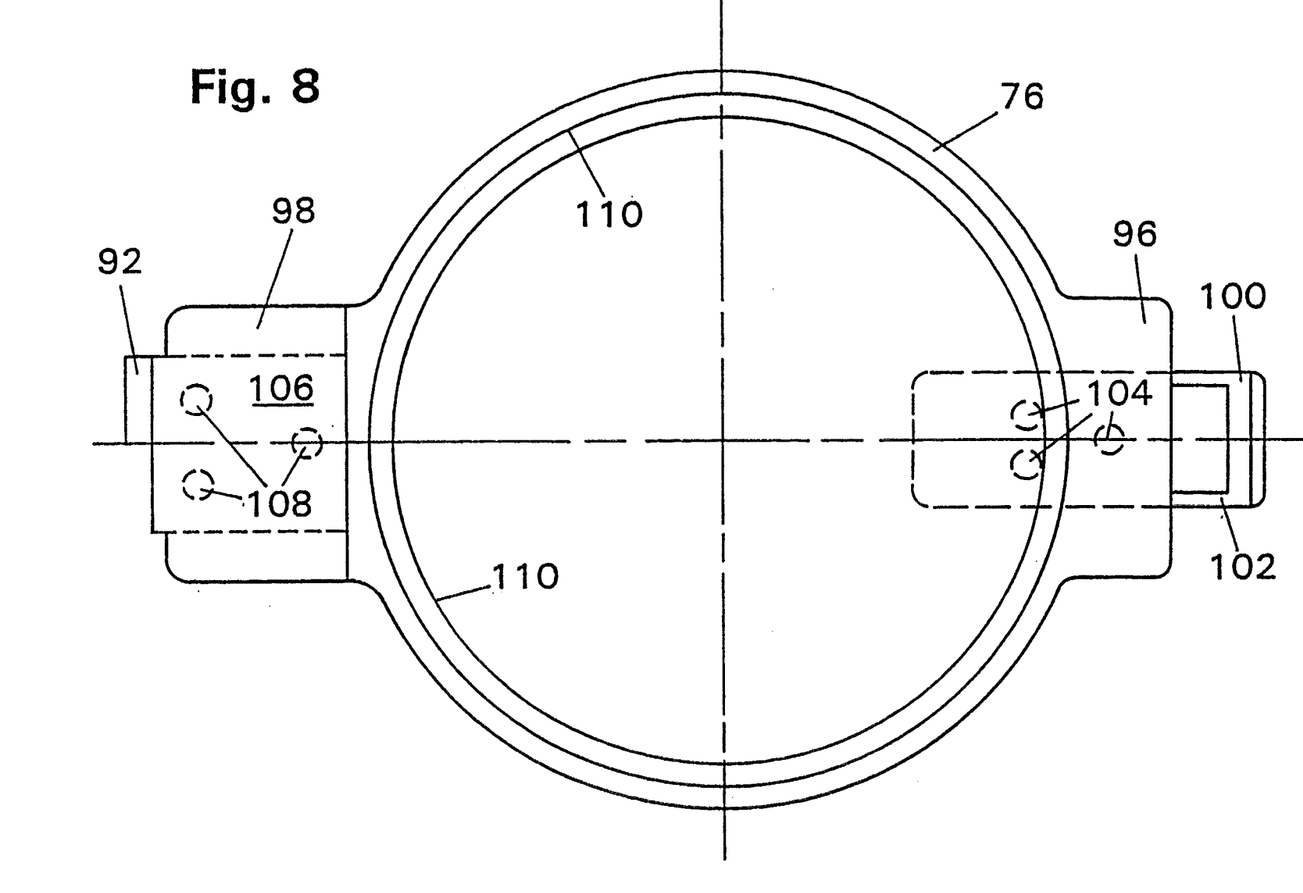
FIG. 8 is a cross-sectional view of the transfer port shown in FIG. 5, taken along lines 8—8 of FIG. 5.
Figure 9:
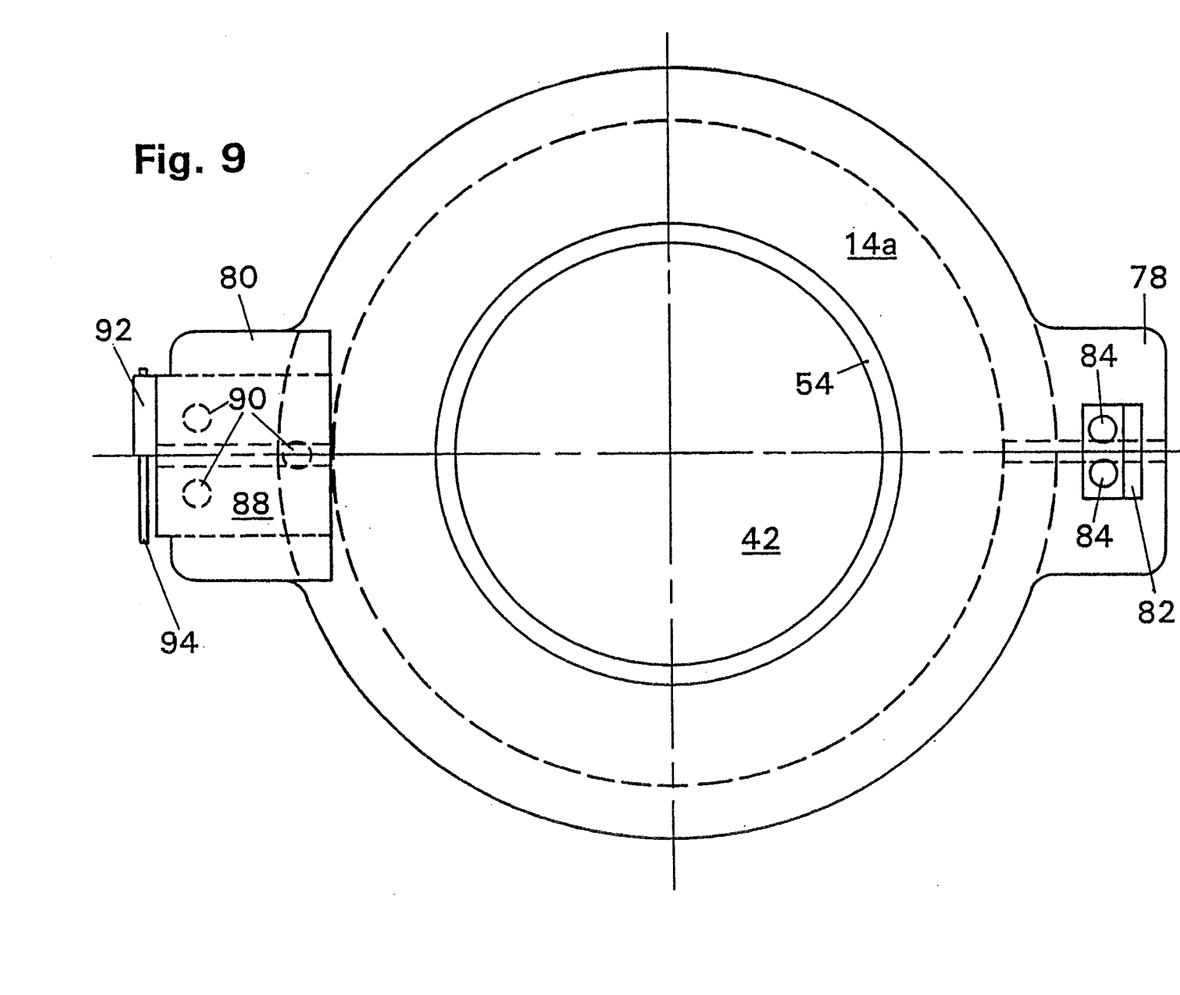
FIG. 9 is a cross-sectional view of the transfer port shown in FIG. 5, taken along lines 9—9 of FIG. 5.

Referring now to FIGS. 5, 8 and 9, there is shown a first door 76 movable between a first position (see FIG. 5) closing the first end 14a of the transfer port 14 to prevent the sterilized elements 12 from being moved into the isolation system 16 and a second position (not shown) opening the first end 14a of the transfer port 14 to allow the sterilized elements 12 to be moved into the isolation system 16. Thus, when the seal 38 is removably mounted across the bore 28 and the first door 76 is in the first position, the seal 38, collar 26, port conduit 42 and first door 76 define a chamber for receiving the treatment medium and when the seal 38 is moved from the first position to the second position and the first door 76 is in the second position, the sterilized elements 12 are movable into the isolation system 16 from the cavity 22 through the opening 24, bore 28 and port conduit 42.

More particularly, as shown in FIG. 9, the first end 14a of the transfer port 14 includes a first mounting member 78 extending radially outwardly from the first end 14a of the transfer port 14 and a second diametrically opposed mounting member 80 extending radially outwardly from the first end 14a of the transfer port 14. The first mounting member 78 includes a catch 82 secured thereto and facing away from the transfer port 14. The catch 82 is secured to the first mounting member 78 by standard bolts 84 in a manner well understood by those skilled in the art.

Similarly, the second mounting member 80 includes a portion of a hinge 86 secured thereto. That is, a first leaf 88 is bolted to the second mounting member 80 by standard bolts 90. At the distal end of the first leaf 88 is a knuckle 92 for receiving a hinge pin 94 in a manner well understood by those skilled in the art. In the present embodiment, it is preferred that the first and second mounting members 78, 80 be formed integrally with the transfer port 14. However, it is understood by those skilled in the art that the first and second mounting members 78, 80 could be separately secured to the transfer port 14, without departing from the spirit and scope of the invention.

As best shown in FIG. 8, the first door 76 is generally disk-shaped and includes a first mounting member 96 extending radially outwardly therefrom and a second mounting member 98 diametrically opposed to the first mounting member and extending radially outwardly from the first door 76. Bolted to the first mounting member 96 is a latch 100 which includes an aperture 102 for receiving the catch 102. The latch 100 is preferably bolted to the exterior of the first door 76 by bolts 104 in a manner that is well understood by those skilled in the art. Similarly, a second leaf 106 is bolted to the second mounting member 98 by bolts 108 for being hingedly secured to the first leaf 88 by the knuckle 92 and hinge pin 94. In this manner, the first door 76 is hingedly mounted to the first end 14a of the transfer port 14 within the isolation system 16. A pair of o-rings 110 are positioned on the inner surface of the first door 76 for engagement with the first end 14a of the transfer port 14. The o-rings 110 provide a tight seal between the first door 76 and the first end 14a of the transfer port 14 when the first door 76 is in the first or closed position.

In the present embodiment, it is preferred that the first door 76 be hingedly secured to the transfer port 14. However, it is understood by those skilled in the art that the first door 76 could be secured to the transfer port 14 in other manners. For instance, the first door 76 could be clamped to the transfer port 14 without departing from the spirit and scope of the invention.

Referring now to FIGS. 1 and 5–7, there is shown a second door 112 movable between a first position closing the second end 26d of the collar 26 with a portion of the bag 20 being disposed between the second door 112 and the second end 26d of the collar 26 and a second position (not shown) away from the second end 26d of the collar 26. The second door 112 is positioned against the second end 14b of the transfer port 14 when a treatment medium is introduced into the transfer port 14 to prevent the seal 38 and bag 20 from being compromised. That is, the second door 112 provides the open end of the collar 26 with structural integrity.

Extending radially outwardly from the second end 58b of the female member 58 is a first mounting member 114. Bolted to the distal end of the first mounting member 114 is a catch 116 by bolts 118 in a manner well understood by those skilled in the art. A second mounting member 120 extends radially outwardly from the second end 58b of the female member 58 at a position diametrically opposite to the first mounting member 114. The second mounting member 120 includes a first leaf 122 bolted to the distal end thereof by bolts 124. A knuckle 126 for receiving a hinge pin 128 (see FIG. 7) are located at the distal end of the first leaf 122 in a manner well understood by those skilled in the art.

Figure 7:
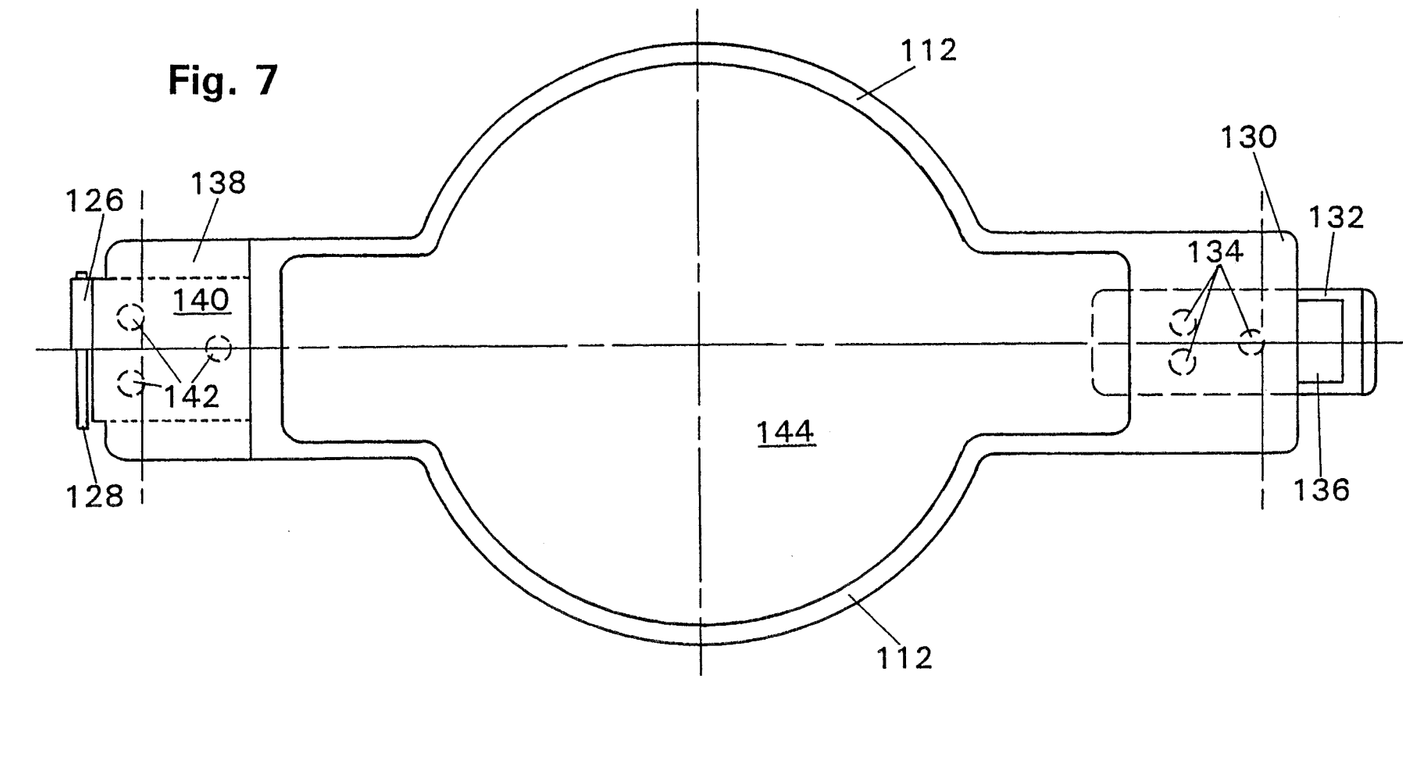
FIG. 7 is a cross-sectional view of the transfer port shown in FIG. 5, taken along lines 7—7 of FIG. 5.

As shown in FIG. 7, the second door 112 is generally disk-shaped and includes a first mounting member 130 extending radially therefrom and including a latch 132 mounted thereon by bolts 134 and including an aperture 136. A second mounting member 138 extends radially outwardly from the second door 112 at a position diametrically opposite to the first mounting member 130 of the second door 112. A second leaf 140 is mounted to the distal end of the second mounting member 138 and is bolted thereto by bolts 142. The second leaf 140 cooperates with the knuckle 126 and hinge pin 128 to hingedly connect the second door 112 to the second end 58b of the female member 58. A rubber gasket 144 is disposed on the interior surface of the second door 112 for engagement with the second end 58b of the female member 58 and the second end 26d of the collar 26 to provide a tight seal.

While in the present embodiment it is preferred that the second door 112 be hingedly mounted to the second end 58b of the female member 58, it is understood by those skilled in the art that the second door 112 can be mounted to the female member 58 or the transfer port 14 in other manners without departing from the spirit and scope of the invention. For instance, the first door 112 could be clamped to the transfer port 14.

In use, the container 10 is shipped to the isolation system 16 in an outer bag (not shown) for protecting the integrity of the bag 20. With the first door 76 in the closed position, and the second door 112 in the open position, the user removes the container 10 from the outer bag and grasps the handles 36. The first end 26c of the collar 26 is then inserted into the second end 14b of the transfer port 14 such that the exterior surface 26b of the collar 26 engages the o-rings 48 to provide a tight seal. As the collar 26 is moved into the transfer port 14, the user aligns the interlocking elements 34 with the profile formed by the second flanges 62 until the interlocking elements 34 are aligned with the grooves 64. The user then rotates the collar 26 to position the interlocking elements 34 in the groove 64 between the second flanges 62 and the first flange 60 to thereby lock the collar 26 to the transfer port 14. The user then closes the second door 112 and hooks the catch 116 on the female member 58 to the latch 132 on the second door 112.

The treatment medium is then introduced into the transfer port 14 through the supply conduit 68 for a period of time necessary to sterilize the chamber defined within the transfer port 14. Any excess steam during this sterilization process is drained through the discharge conduit 70. Once the chamber of the transfer port 14 has been sterilized, the vacuum or drying conduit 74 is then used to remove any of the excess treatment medium from the chamber of the transfer port 14 that did not drain through the discharge conduit 70. The user then opens the first door 76 to gain access to the conduit 42. The user then reaches through a glove port (not shown) into the transfer port 14 or by automation (i.e., robotic control) grasps the pull tab 40 of the seal 38 and removes, opens or separates the seal 38 from the flange 30 of the collar 26. At this point, the sterilized elements 12 can be passed through from the cavity 22 through the opening 24, bore 28, conduit 42 into the isolation system 16 without exposing the sterilized elements 12 to ambient atmosphere or a contaminated region.

The present invention permits the sterilized elements 12 to be transferred to the isolation system 16 in an inexpensive manner. The pharmaceutical industry merely has to purchase one transfer port 14 for each isolation system 16 and as many containers 10 that are needed. After each container 10 is emptied of the sterilized elements 12, the bag 20 and/or collar 26 (if constructed of an inexpensive material) can be discarded or, in today's world of environmental concerns, the bag 20 and/or collar 26 can be returned to the manufacturer for sterilization and refilling. This results in a significant savings to the pharmaceutical industry.

From the foregoing description, it can be seen that the present invention comprises an improved inexpensive device for transferring sterilized elements into an isolation system. It will be appreciated by those skilled in the art, that changes could be made to the embodiment described in the foregoing description without departing from the broad inventive concept thereof. It is understood, therefore, that this invention is not limited to the particular embodiment disclosed, but is intended to cover all modifications which are within the scope and spirit of the invention as defined by the appended claims.

We claim:

1. A combination container for holding sterilized elements and a sterilizable transfer port for transferring the sterilized elements into an isolation system, said isolation system including a wall having an inner surface and defining an interior region and, said combination container comprising:

a flexible bag defining a cavity containing a plurality of sterilized elements, said bag including an opening for removing said sterilized elements from said cavity;

a collar having a first end, a second end, an interior surface and an exterior surface, said interior surface defining a bore extending through said collar, said bag being secured to said collar at said first end with said opening in registry with said bore;

a removable seal movable between a first position wherein said seal initially extends across said bore at said first collar end adjacent said bag to tightly seal the bore and prevent said sterilized elements from being removed from said cavity and to maintain the sterility of said sterilized elements and a second position wherein said seal is moved from said first position to access said cavity such that said sterilized elements are removable from the cavity through said opening and said bore;

a tubular transfer port extending through a wall of an isolation system, said transfer port including a first end, a second end and a port conduit extending between said first and second ends, said collar being in releasable complementary, sealed engagement with said transfer port;

at least one supply conduit in fluid communication with said port conduit for introducing into said port conduit at least one treatment medium; and a first door movable between a first position closing said first end of said transfer port to prevent said sterilized elements from being moved into said isolation system and a second position opening said first end of said transfer port to allow said sterilized elements to be moved into said isolation system whereby when said seal is removably mounted across said bore and said first door is in the first position the seal, collar, port conduit, and first door define a chamber for receiving the treatment medium and when said seal is moved from the first position to the second position and the first door is in the second position, said sterilized elements are movable into said isolation system from said cavity through said opening, bore and conduit.

2. The combination as recited in claim 1, wherein said collar includes a first end and a second end, said bag extending from said second end of said collar and further including a second door movable between a first position opening said second end of said collar with a portion of said bag being disposed between said second door and said second end of said collar and a second position away from said second end of said collar.

3. The combination as recited in claim 1 further including a quick connect device interconnected between said port and said collar for quickly connecting and disconnecting said port and collar.

4. The combination as recited in claim 3 wherein said quick connect device comprises a bayonet quick connection between said collar and said transfer port.

5. The container as recited in claim 1 wherein said collar includes a flange extending radially inwardly and said seal is in partial facing engagement with said flange when said seal is in said first position.

6. The container as recited in claim 5 wherein said seal is releasably adhesively secured to said flange when said seal is in said first position.

7. The container as recited in claim 6 wherein said seal includes a pull tab.

8. The container as recited in claim 1 wherein said collar is generally annular in cross section.

9. A combination container for holding sterilized elements and a sterilizable transfer port for transferring sterilized elements into an isolation system, said isolation system including a wall, said combination comprising:

- a flexible bag defining a cavity containing a plurality of sterilized elements, said bag including an opening for removing said sterilized elements from the cavity;
- a collar having a first end, a second end, an interior surface and an exterior surface, said interior surface defining a bore extending through said collar, said bag being secured to said collar at said first end with said opening in registry with said bore;
- a removable seal movable between a first position wherein said seal initially extends across said bore at said first collar end adjacent said bag to tightly seal the bore and prevent elements from being removed from said cavity and to maintain the sterility of said sterilized elements and a second position wherein said seal is moved from said first position to access the cavity such that said sterilized elements are removable from the cavity through said opening and said bore;
- a tubular transfer port extending through a wall of an isolation system, said transfer port including a first end and a second end, said transfer port having an interior surface and an exterior surface, said interior surface of said transfer port defining a conduit extending between said first and second ends, said collar being in releasable complementary, facing, sealed engagement with said interior surface of said transfer port;
- a quick connect device interconnected between said port and said collar for quickly connecting and disconnecting said port and collar;
- at least one supply conduit and at least one discharge conduit in fluid communication with said port conduit for introducing into and removing from said port conduit at least one treatment medium; and
- a first door movable between a first position closing said first end of said transfer port to prevent said sterilized elements from being moved into said isolation system and a second position opening said first end of said transfer port to allow said sterilized elements to be moved into said isolation system whereby when said seal is removably mounted across said bore and said first door is in the first position the seal, collar, port conduit, and first door define a chamber for receiving the treatment medium and when said seal is moved from the first position to the second position and said first door is in the second position said sterilized elements are movable into said isolation system from said cavity through said opening, bore and port conduit.

* * * * *